United States Patent [19]

Higashide et al.

[11] 4,162,940

[45] Jul. 31, 1979

[54] METHOD FOR PRODUCING ANTIBIOTIC C-15003 BY CULTURING NOCARDIA

[75] Inventors: Eiji Higashide, Takarazuka; Mitsuko Asai, Takatsuki; Seiichi Tanida, Kyoto, all of Japan

[73] Assignee: Takeda Chemical Industries, Ltd., Osaka, Japan

[21] Appl. No.: 811,448

[22] Filed: Jun. 29, 1977

[30] Foreign Application Priority Data

Mar. 31, 1977 [JP] Japan .................................. 52-37166
Apr. 1, 1977 [JP] Japan .................................. 52-37886

[51] Int. Cl.² .............................................. C12D 9/20
[52] U.S. Cl. ..................................... 435/119; 435/872
[58] Field of Search ........................... 195/96, 80 R, 80

[56] References Cited

U.S. PATENT DOCUMENTS 3,896,111  7/1975  Kupchan et al. ................. 260/239 T

OTHER PUBLICATIONS

Journal American Chemical Society, vol. 94, pp. 1354–1356, 5294–5295.
Journal of the Chemical Society, Chemical Communications, 1973, p. 390.

Primary Examiner—Lionel M. Shapiro
Attorney, Agent, or Firm—Wenderoth, Lind & Ponack

[57] ABSTRACT

A novel Antibiotic C-15003 is produced by cultivating a microorganism of the genus Nocardia.

The Antibiotic C-15003 is useful as an antifungal agent or an antiprotozoan agent.

2 Claims, No Drawings

METHOD FOR PRODUCING ANTIBIOTIC C-15003 BY CULTURING NOCARDIA

This invention relates to Antibiotic C-15003, which is a novel antibiotic, a method of producing the same and a method of producing derivatives from said antibiotic.

We collected many soil and other samples and performed a screening of the microorganisms isolated from such samples. It was found, by that screening, that certain of the microorganisms were able to produce a novel antibiotic, that such microorganisms belonged to the genus Nocardia and that by cultivating any of those microorganisms in a suitable medium, it was possible to have said antibiotic accumulated in the cultured broth. It was also found that derivatives could be obtained from said antibiotic. Further studies ensued, resulting in the development of this invention.

This invention is therefore directed to:

(1) Antibiotic C-15003 which has the general formula (I):

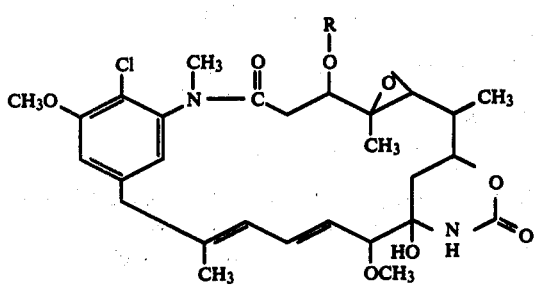

[wherein R represents

—CO—CH$_2$—CH$_2$—CH$_3$ or

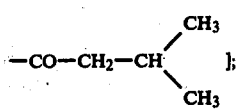

(2) A method of producing Antibiotic C-15003 characterized in that said method comprises cultivating an Antibiotic C-15003-producing strain of the genus Nocardia in a medium to cause the strain to elaborate and accumulate Antibiotic C-15003 in the cultured broth, and recovering said Antibiotic C-15003 from said broth; and (3) A method of producing a compound of the formula (II):

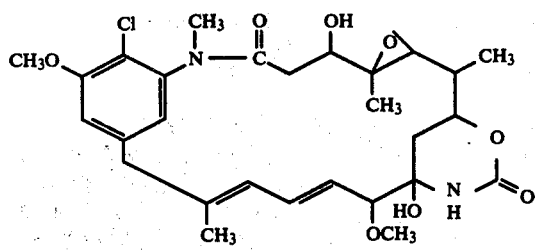

characterized in that said method comprises hydrolyzing Antibiotic C-15003 of the general formula (I):

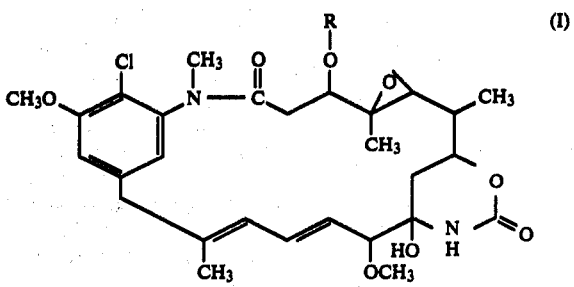

[wherein R represents

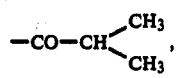

—CO—CH$_2$—CH$_2$—CH$_3$ or

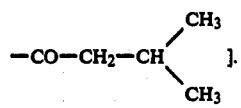

In the context of this invention, the term "Antibiotic C-15003" means, generically, the three compounds having the above general formula (I) as a group, or a mixture of two or three of said compounds or, severally, any of the same compounds. Referring, also, to the general formula (I), the compound in which R is

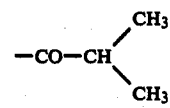

is referred to herein as "Antibiotic C-15003 P-3" or more briefly as "C-15003 P-3"; the compound in which R is —CO—CH$_2$—CH$_2$—CH$_3$ is referred to herein as "Antibiotic C-15003 P-3'" or, more briefly, as "C-15003 P-3'"; the compound in which R is

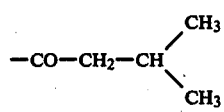

is referred to herein as "Antibiotic C-15003 P-4" or, more briefly, as "C-15003 P-4"; and the compound in which R is H[(general formula (II)] is referred to herein as "Antibiotic C-15003 P-0" or, more briefly, as "C-15003 P-0".

As an example of the Antibiotic C-15003-producing strain of microorganism, there may be mentioned an actinomycete Strain No. C-15003 which we isolated from soil and other samples in our screening for antibiotic-producing microorganisms.

The microbiological characters of Strain No. C-15003 were investigated by procedures analogous to those proposed by Schirling & Gottlieb [International Journal of Systematic Bacteriology 16, 313–340 (1966)]. The results of observations at 28° C. over 21 days are as follows.

(1) Morphological characters

The vegetative mycelium extends well and develops into branches, both on agar and in liquid medium. Many of the hyphae measure 0.8 to 1.2 μm in diameter and, in certain instances, may divide into fragments resembling rod bacteria or branched short lengths of hyphae. The strain gives good growth on various taxonomical media, with aerial mycelium being superimposed on the vegetative mycelium, although it frequently forms coremia like bodies (50–200×200–1000 μm) on which further aerial growth takes place. Many of the aerial mycelia are flexuous, straight or a loosely spiral like configuration being encountered on a few occasions. Microscopic examination of aged cultures reveals that only in few cases the conidia like cells occur in chains, while the cell suspensions obtained from the surfaces of such cultures, as microscopically examined, contained many elongated ellipsoidal (0.8–1.2 μm×4.8–6.8 μm) and ellipsoidal (0.8–1.2×1.0–2.0 μm) bodies resembling arthrospores.

Electron-microscopic examinations showed that these bodies had smooth surfaces.

(2) The constituents of cells

The strain was shake-cultured in modified ISP No. 1 medium at 28° C. for 66 to 90 hours, at the end of which time the cells were collected and rinsed. By the method of B. Becker et al. [Applied Microbiology 12, 421 (1964)] and the method of M. P. Lechevalier. [Journal of Laboratory and Clinical Medicine 71, 934 (1968)], the above whole cells were examined for diaminopimelic acid and sugar composition. The former was found to be the meso-form, while spots were detected which corresponded to galactose and arabinose.

(3) Characteristics on taxonomical media

The strain showed comparatively good growth on various media, with the vegetative mycelium being colorless to pale yellow in initial phases of culture and light yellowish tan to yellowish tan in later phases. The strain produces soluble pigments, yellow to yellowish tan, in various taxonomical media. The aerial mycelium is powdery and generally gives moderate growth, being white to yellow or light yellowish tan. The characteristics of the strain in various taxonomical media are set forth in Table 1.

Table 1 Cultural characteristics of Strain No. C-15003 on taxonomical media (A) Sucrose nitrate agar:
  Growth (G): Moderate, Brite Melon Yellow (3 ia)* to Amber tan (3 lc)*, coremia like bodies formed
  Aerial mycelium (AM): Scant, white
  Soluble pigment (SP): None or pale yellowish tan
(B) Glycerol nitrate agar:
  G: Moderate, Lt Ivory (2 ca)*, coremia like bodies formed
  AM: Moderate, white
  SP: None
(C) Glucose asparagine agar:
  G: Moderate, Brite Marigold (3 pa)* to Brite Yellow (2 pa)*.
  AM: Scant, white
  SP: Brite Yellow (2 pa)*
(D) Glycerol asparagine agar:
  G: Moderate, Lt Ivory (2 ca)*, coremia like bodies formed
  AM: Scant, white
  SP: None
(E) Starch agar:
  G: Moderate, Lt Ivory (2 ca)* to Lt Wheat (2 ea)*, coremia like bodies formed
  AM: Abundant, Lt Ivory (2 ca)*
  SP: None
(F) Nutrient agar:
  G: Moderate, Lt Ivory (2 ca)* to Colonial Yellow (2 ga)*, coremia like bodies formed
  AM: Scant, white
  SP: None
(G) Calcium malate agar:
  G: Moderate Lt Ivory (2 ca)* to Lt Wheat (2 ea)*, coremia like bodies formed.
  AM: Moderate, white to Lt Ivory (2 ca)*
  SP: None
(H) Yeast extract-malt extract agar:
  G: Moderate, Amber (3 lc)* to Brite Yellow (3 la)*, coremia like bodies formed
  AM: Moderate, white to Lt Ivory (2 ca)*
  SP: None
(I) Oatmeal agar:
  G: Moderate, Lt Ivory (2 ca)* to Colonial Yellow (2 ga)*, coremia like bodies formed
  AM: Scant, white to light yellow
  SP: None
(J) Peptone yeast extract iron agar:
  G: Moderate, Colonial Yellow (2 ga)*
  AM: None
  SP: Colonial Yellow (2 ga)*
(K) Tyrosine agar
  G: Moderate, Lt Ivory (2 ca)* to Lt Melon Yellow (3 ea)*, coremia like bodies formed.
  AM: Moderate, white to Lt Ivory (2 ca)*.
  SP: Camel (3 ie)*

* The color codes according to Color Harmony Manual, 4th ed. (Container Corporation of America, 1958).

(4) Physiological characters

The physiological characters of the strain are shown in Table 2. Temperature range for growth: 12° C. to 38° C. The temperature range in which good aerial growth occurs on agar (ISP No. 2) is 20° to 35° C.

Table 2 The physiological characters of Strain No. C-15003

Temperature range for growth: 12° to 38° C.
Temperature range for aerial growth: 20° to 35° C.
Liquefaction of gelatin: Positive
Hydrolysis of starch: Positive
Reduction of nitrates: Positive
Peptonization of milk: Positive
Coagulation of milk: Negative
Decomposition of casein: Positive
Production of melanoid pigments:
  Negative (peptone yeast extract iron agar), positive (tyrosine agar)
Decomposition of tyrosine: Positive
Decomposition of xanthine: Negative
Decomposition of hypoxanthine: Negative
Tolerance to lysozyme: Positive
Tolerance to sodium chloride: 2%

(5) Utilization of various carbon sources

The utilization of various carbon sources was investigated using a medium described in Pridham and Gottlieb [Journal of Bacteriology 56, 107 (1948)] and a basal medium of the same composition plus 0.1% of yeast extract. The resultant spectrum is shown in Table 3.

Table 3

| The utilization of carbon sources by Strain No. C-15003 | | | |
|---|---|---|---|
| Source of carbon | Growth | Sources of carbon | Growth |
| D-Xylose | + + +* | Raffinose | ± ±* |
| L-Arabinose | + + | Melibiose | + + |
| D-Glucose | + + + + | i-Inositol | − − |
| D-Galactose | + + | D-Sorbitol | − − |
| D-Fructose | + + + + + | D-Mannitol | + + + + |
| L-Rhamnose | + + | Glycerol | − ± |
| D-Mannose | + + + + + | Soluble starch | + + |
| Sucrose | + + + + | Control | − − |
| Lactose | − −* | | |
| Maltose | ± + | | |
| Trehalose | + + + | | |

*Basal medium with 0.1 % yeast extract added
Note: + + +: Luxuriant growth
+ +: Good growth
+: Growth
±: Poor growth
−: No growth (6) Other characteristics The cells were harvested by the procedure previously described in (2) and DNA was prepared by a procedure analogous to that of J. Marmur et al. [Journal of Molecular Biology 3, 208, 1961]. The G-C (Guanine-Cytosine) content of the DNA was found to be about 71 mole %.

Gram-staining of the vegetative mycelium of this strain was positive.

The above characteristics of Strain No. C-15003 were compared with the descriptions in S. A. Waksman's "The Actinomycetes Vol. 2" [The Williams and Wilkins co., 1961]; R. E. Buchanan and N. E. Gibbons, "Bergey's Manual of Determinative Bacteriology, 8th ed, 1974"; and other literatures.

Whilst this strain was thought to belong to Group III of the genus Nocardia, the failure to find any species having the characters so far described among the known strains led us to conclude that this strain represented a novel species of microorganism.

The present Strain No. C-15003 has been deposited at Fermentation Research Institute, Agency of Industrial Science and Technology (FERM) under the receipt number of 3992; at The Institute for Fermentation, Osaka (IFO) under the accession number of IFO 13726 and at The American Type Culture Collection (ATCC), Maryland, U.S.A. under the accession number of 31281.

While Strain No. C-15003 is a novel species of the genus Nocardia as just mentioned, it is liable, as are microorganisms generally, to undergo variations and mutations, either spontaneously or under the influence of a mutagen. For example, the many variants of the strain which are obtainable by irradiation with X-rays, gamma rays, ultraviolet light, etc., by monocell isolation, by culture on media containing various chemicals, or by any other mutagenic treatment, as well as the mutants spontaneously derived from the strain, should not be considered to represent any other distinct species but, rather, any of such variants and mutants capable of elaborating C-15003 P-3, P-3' and/or P-4 may be invariably utilized for the purposes of this invention. By way of example, subjecting Strain No. C-15003 to various mutagenic treatments yields mutants substantially lacking the ability to produce soluble pigments, mutants with substrate mycelia which are colorless, yellowish green, reddish tan or orange-red, mutants whose hyphae are ready to fragment into bacillary elements or branched short hyphal fragments, and mutants with abundant white aerial mycelia or substantially without aerial mycelia.

The medium employed for the cultivation of such an Antibiotic C-15003-producing strain may be whichever of a liquid and a solid medium only if it contains nutrients which the strain may utilize, although a liquid medium is preferred for high-production runs. The medium may comprise carbon and nitrogen sources which Strain No. C-15003 may assimilate and digest, inorganic matter, trace nutrients, etc. As examples of said carbon sources may be mentioned glucose, lactose, sucrose, maltose, dextrin, starch, glycerol, mannitol, sorbitol, etc., fats and oils (e.g. soybean oil, lard oil, chicken oil, etc.) and so forth. The nitrogen sources may for example be meat extract, yeast extract, dried yeast, soybean meal, corn steep liquor, peptone, cottonseed flour, spent molasses, urea, ammonium salts (e.g. ammonium sulfate, ammonium chloride, ammonium nitrate, ammonium acetate, etc.) and so forth. The medium may further contain salts of sodium, potassium, calcium, magnesium, etc. salts of iron, manganese, zinc, cobalt, nickel, etc., salts of phosphoric acid, boric acid, etc., and organic acid salts such as acetates and propionates. Further, the medium may contain, as added, various amino acids (e.g. glutamic acid, aspartic acid, alanine, glycine, lysine, methionine, proline, etc.), peptides (e.g. dipeptides, tripeptides, etc.), vitamins (e.g. $B_1$, $B_2$, nicotinic acid, $B_{12}$, C, E, etc.), nucleic acids, (e.g. purine, pyrimidine and derivatives thereof) and so forth. For the purpose of adjusting the pH of the medium, there may be added an inorganic or organic acid, alkali, buffer or the like. Suitable amounts of oils, fats, surfactants, etc. may also be added as antifoams.

The cultivation may be conducted by any of the stationary, shake, submerged aerobic and other cultural conditions. For high production runs, submerged aerobic culture is of course preferred. While the conditions of culture, of course, depends upon the condition and composition of medium, the strain, cultural method and other factors, it is normally preferred to carry out incubation at 20° to 35° C. with an initial pH of about 7.0 or thereabouts. Particularly desirable is a temperature from 23° to 30° C. in an intermediate stage of cultivation, with an initial pH of 6.5 to 7.5. While the incubation time also is variable according to the same factors as mentioned above, it is advisable to continue the incubation until the titer of the desired antibiotic product becomes maximal. In the case of shake culture or aerobic submerged culture in liquid medium, the time required normally ranges from about 48 to 144 hours.

The potency of the antibiotic was assayed with *Tetrahymena pyriformis* W as an assay organism. Thus, the above microorganism was grown on a test medium [20 g of Proteose-peptone (Difco), 1 g of yeast extract (Difco), 2 g of glucose, 1000 ml of distilled water and 10 ml of 1M-phosphate buffer (pH 7.0)] at 28° C. for 44 to 48 hours and the potency of the antibiotic was determined by the serial dilution method with a monitering of the turbidity of growth, effect on ascites tumor cells and by a thin-layer chromatographic (briefly TLC) assay to be described hereinafter.

The novel Antibiotic C-15003 P-3, P-3' and/or P-4 is produced and accumulated in the resultant fermentation broth, both extracellularly and intracellularly.

These substances have also been detected by TLC. Thus, the fermentation broth is separated into cells and filtrate by filtration or centrifugation and the filtrate is extracted with the same volume of ethyl acetate. To the cells is added the same amount of 70% acetone-water as the filtrate and, after an hour's stirring at 20° C., the suspension is filtered. The acetone is removed from the filtrate and the resultant aqueous filtrate is extracted with ethyl acetate. Each of the extracts is concentrated to 1/100 by volume and subjected to thinlayer chromatography on a silica gel-glass plate (Merck, West Germany, Kieselgel 60 F 254, 0.25 mm, 20×20) (solvent system: chloroform-methanol=9:1). The potency was determined on the basis of the intensity of spots detected by irradiation with ultraviolet light at 2537 A.

Because C-15003 P-3, P-3' and/or P-4, which are thus produced in the fermentation broth, are lipophyl neutral substances, they can be conveniently recovered by separation and purification procedures which are normally employed for the harvest of such microbial metabolites. For example, there may be employed a procedure which utilizes the difference in solubility between the antibiotic and impurity, means which utilizes the adsorptive affinity of various adsorbents such as activated carbon, macroporous nonionic resins, silica gel, alumina, etc., a procedure of removing the impurities by means of ion exchange resins, and so forth, as applied singly or in a suitable combination or as applied in repetition.

Since, as aforesaid, C-15003 P-3, P-3' and P-4 occur in both the filtrate and cells, the antibiotics are separated and purified by means of such an adsorbent, if one is employed, either directly or after a solvent extraction in the case of the filtrate, or after a solvent extraction in the case of microbial cells. The solvent extraction may be performed by any of the following and other methods e.g. (1) solvent extraction from the culture broth prior to separation of cells and (2) solvent extraction of the cells and the filtrate obtained by filtration, centrifugation or other process. To extract the filtrate and cells independently, the following procedure may be taken advantageously.

The solvents suitable for extraction of the filtrate are water-immiscible organic solvents such as fatty acid esters, e.g. ethyl acetate and amyl acetate; alcohols, e.g. butanol; halogenated hydrocarbons, e.g. chloroform; and ketones, e.g. methyl isobutyl ketone. The extraction is carried out at a pH near neutral and, preferably, the culture fluid previously adjusted to pH 7 is extracted with ethyl acetate. The extract is washed with water and concentrated under reduced pressure. Then, a nonpolar solvent such as petroleum ether or hexane is added to the concentrate and the crude product I containing the active compound is recovered. Because, on TLC, a number of spots are detected in addition to Antibiotic C-15003, the product I is sequentially subjected to the following purification procedures. Thus, as a routine purification procedure, adsorption chromatography is useful and, for this purpose, one of those common adsorbents such as silica gel, alumina, macroporous nonionic adsorbent resin, etc. may be employed. For purification from the crude product I, silica gel is most useful. And development may be carried out, for example starting with petroleum ether and hexane and elution of Antibiotic C-15003 is performed by the addition of a polar solvent such as ethyl acetate, acetone, ethanol or methanol. In a typical process, using silica gel (Merck, West Germany, 0.05–0.2 mm) as a carrier, column chromatography is carried out with a serial increase in the hexane to ethyl acetate ratio. The eluate is sampled and investigated by TLC and the fractions containing C-15003 are pooled and concentrated under reduced pressure. Then, petroleum ether or hexane is added to the concentrate, whereby the crude product II is obtained. Since this product still contains impurities, it is further purified as follows. For example, the product II may be purified by means of a second silica gel column using a different solvent system. The developing system for this purpose may consist in a halogenated hydrocarbon such as dichloromethane or chloroform, with the addition of a polar solvent such as an alcohol, e.g. methanol or ethanol, a ketone, e.g. acetone or methyl ethyl ketone, or the like. In this way, Antibiotic C-15003 is isolated. The order of solvent systems for the first and second silica gel columns may be reversed and, in addition, ordinary organic solvents may be used in conjunction with the above systems if necessary.

Where a macroporous adsorbent resin is used as purification means for crude product II, elution of Antibiotic C-15003 is accomplished with a mixture of water with a lower alcohol, a lower ketone or an ester. The lower alcohol may for example be methanol, ethanol, propanol or butanol and the lower ketone may for example be acetone or methyl ethyl ketone. The ester may for example be ethyl acetate. In a typical procedure, the crude product II is dissolved in 60% methanol-water and adsorbed on a column of Diaion HP-10 (Mitsubishi Kasei K.K.). The column is washed with 70% methanol-water and, then, elution is carried out with 90% methanol-water. In this way, Antibiotic C-15003 is eluted from the column.

In either of the processes described above, the fractions containing Antibiotic C-15003 are pooled and concentrated under reduced pressure. To the dry product is added 5 to 8 volumes of ethyl acetate and the mixture is allowed to stand, whereupon crystals of Antibiotic C-15003 separate. These crystals contain C-15003 P-3, P-3' and P-4. These compounds are then separated from each other by means of an adsorbent such as those mentioned hereinbefore. Thus, using silica gel or a macroporous nonionic adsorbent resin and the above solvents, the desired compounds may be fractionally eluted. When, for example, silica gel is employed, development is carried out with hexane, ethyl acetate, or chloroform-methanol, whereby C-15003 P-4, P-3' and P-3 emerge in that order. After detection by TLC, the fractions corresponding to C-15003 P-4, P-3' and P-3 are respectively concentrated under reduced pressure and ethyl acetate is added to the concentrates. In this manner, the respective compounds can be obtained as crystals. When a macroporous nonionic adsorbent resin is employed, gradient elution with a varying ratio of alcohol, ketone or ester to water may be utilized. For example, by the gradient elution method involving the use of 60% methanol-water and 95% methanol-water, with 5% sodium chloride added, C-15003 P-3, P-3' and P-4 merge in the order mentioned. After sampling and detection by TLC, each group of active fractions is concentrated under reduced pressure and crystallized from ethyl acetate. The isolated crystals include ethyl acetate as a solvent of crystallization and, after drying over phosphorus pentoxide at 70° C. for 8 hours, show the following physical and chemical properties. (Table 4).

Table 4

|  | Antibiotic C-15003 | | |
|---|---|---|---|
|  | P - 3 | P - 3' | P - 4 |
|  | $C_{32}H_{43}ClN_2O_9 = 635.169$ | $C_{32}H_{43}ClN_2O_9 = 649.196$ |  |
| Melting Point(°C.) | 190–192° | 182–185° | 177–180° |
| Specific rotation | −136° ± 10° | −134°± 10° | −142°± 10° |
| $[\alpha]_D^{22°}$ (C = 0.375 CHCl₃) | (C = 0.11 CHCl₃) | (C = 0.522 CHCl₃) |  |
| Elemental analysis  C | 60.6 | .09 | 60.65 |
|   H | 7.04 | 7.02 | 7.05 |
| Found (%)  N | 4.33 | 4.34 | 4.25 |
|   Cl | 5.37 | 5.99 | 5.23 |
| Elemental analysis  C | 60.51 | 60.51 | 61.05 |
|   H | 6.82 | 6.82 | 6.99 |
| Calcd.(%)  N | 4.41 | 4.41 | 4.32 |
|   Cl | 5.58 | 5.58 | 5.46 |
| Ultraviolet absorption spectra nm(ε) (in methanol) | 233(30250) 240(sh 28450) 252(27640) 280(5750) 288(5700) | 233(30155) 240(sh 28250) 252(27600) 280(5750) 288(5700) | 233(29900) 240(sh 28240) 252(27590) 280(5712) 288(5680) |
| Infrared absorption spectra (cm⁻¹)KBr | 1740, 1730, 1670, 1580 1445, 1385, 1340, 1255 1180, 1150, 1100, 1080, 1038 | 1740, 1730, 1670, 1580, 1445, 1385, 1340, 1255, 1180, 1150, 1100, 1080, 1038 | 1740, 1730, 1670, 1580 1445, 1385, 1340, 1255 1180, 1150, 1100, 1080, 1038 |
| Nuclear magnetic resonance spectra (ppm) 100MHz in CDCl₃ | 1.27(d) (3H) 1.28(d) (3H) | 1.06(t) (3H) | 1.03(d) (6H) |
| Mass spectra(m/e) | 573, 485, 470, 450 | 573, 485, 470, 450 | 587, 485, 470, 450 |
| Solubility | Insoluble in petr.ether, hexane & water. Sparingly soluble in benzene & ether.. Soluble in chloroform, ethyl acetate, acetone, ethanol, methanol, pyridine, tetrahydrofuran & dimethylsulfoxide | Insoluble in petr.ether, hexane & water. Sparingly soluble in benzene & ether. Soluble in chloroform, ethyl acetate, acetone, ethanol, methanol, pyridine, tetrahydrofuran & dimethylsulfoxide | Insoluble in petr.ether, hexane & water. Sparingly soluble in benzene & ether. Soluble in chloroform, ethyl acetate, acetone, ethanol, methanol, pyridine, tetrahydrofuran & dimethylsulfoxide. |
| Color reactions | Dragendorff: Positive Beilstein: Positive | Dragendorff: Positive Beilstein: Positive | Dragendorff: Positive Beilstein: Positive |

Based on the above molecular formula shown above and the antimicrobial and antitumor activity data given hereinafter, the present antibiotic was compared with the known groups of antibiotics. The literature search failed to locate no distinct group similar to Antibiotic C-15003. However, a search for substances that might give ultraviolet absorptions similar to those of the present antibiotic among component of plant and other naturally-occurring organic compounds led us to the maytanacine groups and, based on the molecular formulas involved, in particular, it was assumed that the antibiotic belongs to the maytanacine group of compounds containing two nitrogen atoms. Maytanacine was obtained as a component of plant and was reported in Journal of American Chemical Society 97, 5294(1975). The mass spectrum of maytanacine is as follows.

| M⁺-(a) | M⁺-(a+b) | 485-CH₃ | 485-Cl |
|---|---|---|---|

-continued

| 545 | 485 | 470 | 450 |
|---|---|---|---|
| (a)=H₂O + HNCO |  |  | 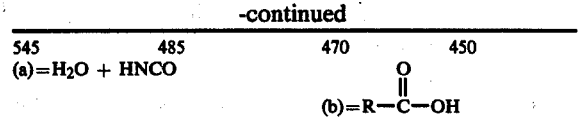 |

The presence of m/e 485, 470 and 450 for C-15003 P-3, P-3' and P-4 convinces us at once that these compounds have a skeletal structure identical with that of maytanacine, differentiating them from maytanacine in the kind of acyl group in 3-position. It is thus clear that Antibiotic C-15003 is a novel compound. When C-15003 P-3, P-3' and P-4 were each degradated with alkali and analyzed by gas chromatography for the liberated carboxylic acids, it was found that isobutyric acid, butyric acid and isovaleric acid were obtainable from C-15003 P-3, C-15003 P-3' and C-15003 P-4, respectively. FIG. 1 shows the structures, based on the above data, of C-15003 P-3, P-3' and P-4. FIG. 1

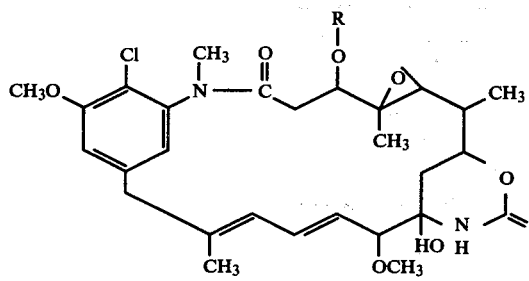 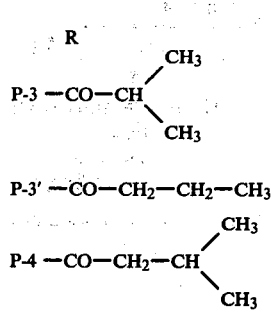

Biological Activity (A) Antimicrobial activity:

With trypticase-soy agar (BBL) as an assay medium, the inhibitory concentrations against the microorganisms named below were investigated by the paper disc method. Thus, filter-paper discs (Toyo Seisakusho, thin-type, 8 mm dia.) each impregnated with 0.02 ml of a 300 μg/ml solution of C-15003 P-3, P-3' or P-4 were placed on plates respectively inoculated with the microorganisms named below to investigate the minimal inhibitory concentrations. The results showed that the antibiotics had no activity against the following microorganisms.

*Escherichia coli, Proteus vulgaris, Proteus mirabilis, Pseudomonas aeruginosa, Staphylococcus aureus, Bacillus subtilis, Bacillus cereus, Klebsiella pneumoniae, Serratia marcescens, Mycobacterium avium*

On the other hand, with agar plates containing the assay medium [3.5 g disodium hydrogen phosphate, 0.5 g monopotassium dihydrogen phosphate, 5 g yeast extract (Difco), 10 g glucose, 15 g agar, 1000 ml distilled water, pH 7.0], the growth inhibition against *Talaromyces avellaneus* was assayed. In this assay, the minimal inhibitory concentrations were 3 μg/ml for C-15003 P-3 and P-3', and 1.5 μg/ml for C-15003 P-4. Furthermore, the wild strain of *Tetrahymena pyriformis* W as an assay organism was cultivated on an assay medium [composed of 20 g Proteose-peptone (Difco), 1 g yeast extract, 2 g glucose, 1000 ml distilled water and 10 ml 1 M-phosphate buffer pH 7.0] at 28° C. for 44 to 48 hours and the growth inhibitory activity of the antibiotic compounds against this particular microorganism was determined by the serial dilution method. Growth inhibition occurred at 1 μg/ml for C-15003 P-3 and P-3', and at 0.5 μg/ml for C-15003 P-4.

Anti-fungal activity is shown in Table 5. As seen from Table 5, C-15003 has growth inhibitory activity against microorganisms which cause plant diseases. The filter-paper discs impregnated with 0.02 ml of a 1000 μg/ml solution of C-15003 were placed on plates respectively inoculated with the microorganisms as following Table 5.

Table 5

| Test organisms | Anti-microbial spectra | | | |
|---|---|---|---|---|
| | IFO number | medium | hour | Inhibition diameter |
| Alternaria kikuchiana | 7515 | PSA* | 48 | 38 |
| Fusicladium levieri | 6477 | PSA* | 90 | 68 |
| Helminthosporium sigmoideum var. irregulare | 5273 | PSA* | 48 | 55 |

Table 5-continued

| Test organisms | Anti-microbial spectra | | | |
|---|---|---|---|---|
| | IFO number | medium | hour | Inhibition diameter |
| Pyricularia oryzae | — | PSA* | 48 | 53 |
| Elsinoe fawcetti | 8417 | PSA* | 90 | 55 |
| Fusarium oxysporum f. cucumerinum | — | PSA* | 48 | 20 |
| Guignardia laricina | 7888 | PSA* | 48 | 12 |
| Cochlioborus miyabeanus | 5277 | PSA* | 48 | 60 |
| Diaporthe citri | 9170 | PSA* | 48 | 55 |
| Gibberella zeae | 8850 | PSA* | 48 | 37 |
| Sclerotinia sclerotiorum | 9395 | PSA* | 90 | 65 |
| Venturia pirina | 6189 | PSA* | 48 | 50 |
| Pellicularia sasakii | 9253 | PSA* | 48 | 50 |
| Pythium aphanidermatum | 7030 | PSA* | 48 | 58 |
| Botrytis cinerea | — | PSA* | 48 | 48 |
| Aspergillus niger | 4066 | PSA* | 48 | 0 |
| Penicillium chrysogenum | 4626 | PSA* | 48 | 35 |
| Rhizopus nigricans | 6188 | PSA* | 48 | 25 |
| Saccharomyces cerevisiae | 0209 | PSA* | 48 | 0 |
| Rhodotorula rubra | 0907 | PSA* | 48 | 28 |
| Trichophyton rubrum | 5467 | GB** | 48 | 38 |
| Trichophyton mantagrophytes | 7522 | GB** | 48 | 38 |
| Candida albicans | 0583 | GB** | 48 | 0 |
| Candida utilis | 0619 | GB** | 48 | 0 |
| Cryptococcus neoformans | 0410 | GB** | 48 | 43 |

*PSA: Potato sucrose agar medium
**GB: Glucose nutrient agar medium (B) Antitumour activity The therapeutic effects of C-15003 P-3, P-3' and P-4 (dosed intraperitoneally for 9 consecutive days) upon P388 leukemia in mice ($1 \times 10^6$ cells/animal, mouse, intraperitoneally transplanted) were investigated. The results showed that, in terms of life span-extending ratio, these compounds had an antitumour activity as high as 200% at the dose level of 0.00625 mg/kg/day.

(C) Toxicity

In an acute toxicity test with mice as test animals, which involved intraperitoneal injections of C-15003 P-3, P-3' and P-4, all of these antibiotics showed a $LD_{50}$ value more than 0.313 mg/kg.

As mentioned hereinbefore, the present Antibiotic C-15003 has strong inhibitory activity against fungi and protozoa and, therefore, is of value as an antifungal or antiprotozoan agent. Furthermore, because Antibiotic C-15003 displays a life span-extending action upon tumour-bearing mammalian animals (e.g. mouse), it is also expected that the compound will be of use as an antitumour drug.

Antibiotic C-15003, as an antifungal and antiprotozoan agent, can be used with advantage for an assessment of the bacterial ecology in the soil, active sludge, animal body fluid or the like. Thus, when valuable bacteria are to be isolated from soil samples or when the actions of bacteria are to be evaluated independently of those of fungi and protozoa in connection with the operation and analysis of an active sludge system used in the treatment of waste water, as the present antibiotic may be utilized to obtain a selective growth of the bacterial flora without permitting growth of the concomitant fungi and protozoa in the specimen. In a typical instance, the sample is added to a liquid or solid medium and 0.1 ml of a 10 to 100 μg/ml solution of the antibiotic in 1% methanol-water is added per ml of the medium, which is then incubated.

The present Antibiotic C-15003 can also be used as an anti-microbial agent for the treatment of plant diseases caused by the microorganisms mentioned in the above Table 5.

In the typical application, Antibiotic C-15003 is used in a form of 1% methanolic aqueous solution containing 0.5 μg/ml–5 μg/ml of the antibiotic. For instance Antibiotic C-15003 may be used for the control of the reddish brown sheath rot, the blast, the Helminthosporium leaf spot and the sheat blight of rice plants.

It is thus apparent that C-15003 P-3, P-3' and P-4 are all novel compounds having the same skeletal structure and can be used also as intermediates for the production of other pharmaceutically useful commpounds. Thus, by way of deacylation reaction, P-15003 P-0 [maytansinol] with a hydroxyl group in 3-position can be derived from the present antibiotic. In this connection, because the acyl group is in position beta to carbonyl, the conventional reductive hydrolysis reaction can be employed with advantage. Thus, by means of a complex metal hydride [e.g. lithium aluminum hydride (LiAlH$_4$)] at a low temperature (e.g. $-20°$–$0°$ C.), the O-ester bond in 3-position may be hydrolytically cleaved, without affecting other functional groups, e.g. carbonyl, epoxy, carbon-carbon double bonds, etc., to yield maytansinol. The physical and chemical data on this maytansinol sample thus obtained is in good agreement with the data given in Kupchan et al The Journal of American Chemical Society 97, 5294–5215(1975)].

The following examples are further illustrative but by no means limitative of the invention, wherein "part(s)" is based on weight unless otherwise noted and the relationship between "part(s)" and "part(s) by volume" corresponds to that between "gram(s)" and "milliliter(s)", and "%" is based on "weight/volume" unless otherwise noted.

EXAMPLE 1

Nocardia No.C-15003 (IFO 13726; FERM 3992; ATCC 31281) as grown on a medium (yeast extract-malt extract agar) was used to inoculate a 200 parts by volume fermenter containing 40 parts by volume of a seed culture medium (2% glucose, 3% soluble starch, 1% raw soybean meal, 1% corn steep liquor, 0.5% Polypepton, 0.3% NaCl, 0.5% CaCO$_3$, pH 7.0). The inoculated medium was incubated at 28° C. for 48 hours to obtain an inoculum. A 0.5 part by volume portion of the inoculum thus obtained was transferred to a 200 parts by volume fermenter containing 40 parts by volume of a fermentation medium composed of 5% dextrin, 3% corn steep liquor, 0.1% Polypepton and 0.5% CaCO$_3$ (pH 7.0), and cultivated at 28° C. for 90 hours to give inoculum (seed culture).

As determined by the serial dilution method using Tetrahymena pyriformis W as an assay organism and Antibiotic C-15003 P-3 as the standard sample, the above culture was found to have a titer of 25 μg/ml.

EXAMPLE 2

A 10 parts by volume portion of the inoculum (seed) obtained in Example 1 was transferred to a 2000 parts by volume fermenter containing 500 parts by volume of a seed culture medium (same as above) and incubated at 28° C. for 48 hours. A 500 parts by volume portion of the resultant culture was transferred to a 50,000 parts by volume tank of stainless steel containing 30,000 parts by volume of seed culture medium and cultivated at 28° C., under aeration (30,000 parts by volume/min.), agitation [280 r.p.m. (½DT)] and internal pressure (1 kg/cm$^2$) to obtain a seed culture. This culture was used to seed a 200,000 parts by volume tank of stainless steel containing 100,000 parts by volume of a fermentation medium similar to the one used in Example 1 at an inoculation rate of 10%. The inoculated medium was incubated at 28° C., under aeration (100,000 parts by volume/min.), agitation [200 r.p.m.(½ DT)] and internal pressure (1 kg/cm$^2$) for 90 hours. As determined by the same procedure as that described in Example 1, the culture obtained above was found to have a titer of 25 μg/l.

EXAMPLE 3

To 95,000 parts by volume of the culture obtained in Example 2 was added 2,000 parts of Hyflo-supercel ® (Johnes and Manville Products, U.S.A.) and, after thorough mixing, the mixture was filtered on a pressure filter to obtain 85,000 parts by volume of filtrate and 32,000 parts of moist cells. The filtrate 85,000 parts by volume was stirred and extracted with 30,000 parts by volume of ethyl acetate. This procedure was repeated once again. The ethyl acetate layers were pooled, washed twice with 30,000 parts by volume portions of water, dried by the addition of 500 parts of anhydrous sodium sulfate and concentrated under reduced pressure to 200 parts by volume. Petroleum ether was added to the concentrate and the resultant precipitate was recovered by filtration (53 parts). This crude product I was stirred with 100 parts by volume of ethyl acetate and the insolubles were filtered off. The filtrate was stirred with 10 parts of silica gel (Merck, West Germany, 0.05–0.2 mm) and the ethyl acetate was removed under reduced pressure. The residue was applied to the top of a silica gel column (400 parts by volume). Elution was carried out with 500 parts by volume of hexane, 500 parts by volume of hexane-ethyl acetate (3:1), 500 parts by volume of hexane-ethyl acetate (1:1), 500 parts by volume of hexane- ethyl acetate (1:3), 500 parts by volume of ethyl acetate and 1,000 parts by volume of ethyl acetate-methanol (50:1), with the eluate being collected in 100 parts by volume fractions.

One part of volume portion of each fraction was concentrated to dryness, and 0.1 part by volume of ethyl acetate was added to the concentrate to give a mixture. The mixture was spotted at 2.5 cm from the bottom edge of a silica gel-glass plate (Merck, West Germany, 60 F $_{254}$, 0.25 mm, 20×20) and developed or about 17 cm with a solvent system of ethyl acetate-methanol (19:1). After development, detection was carried out with ultraviolet light (2537Å).

The active fractions No. 23-No.28 of Rf0.6–0.65 were collected and concentrated under reduced pressure to about 20 parts by volume. To this concentrate was added 150 parts by volume of petroleum ether to obtain 15 parts of a crude product II.

EXAMPLE 4

With stirring, 32,000 parts of the moist cells obtained in Example 3 were extracted with 50,000 parts by volume of 70% acetone-water for 3 hours and, then, filtered on a pressure filter. The extraction with 50,000 parts by volume of 70% acetone-water and subsequent filtration was repeated once again. The filtrates were pooled and the acetone was removed by concentration under reduced pressure. The resultant aqueous system was passed through a column of 5,000 parts by volume Diaion HP-10 (Mitsubishi Kasei K.K.). The column was washed with 20,000 parts by volume of water and 50% aqueous methanol, followed by elution with 15,000 parts by volume of 90% methanol-water. The eluate was concentrated under reduced pressure to 3,000 parts by volume and shaken with 3,000 parts by volume of water and 3,000 parts by volume of ethyl acetate. The above procedure was repeated once again. The ethyl acetate layers were combined, washed with water, dried by the addition of anhydrous sodium sulfate and concentrated under reduced pressure to 200 parts by volume. Following the addition of petroleum ether, the precipitate was recovered by filtration (28 parts). The above product was purified by means of a column of silica gel to recover 8.0 parts of crude product II.

EXAMPLE 5

In 10 parts by volume of ethyl acetate was dissolved 1.5 parts of the crude product II obtained in Example 3 and the solution was stirred well with 4 parts of silica gel (Merck, West Germany, 0.05–0.2 mm). The ethyl acetate was removed under reduced pressure. The residue was applied to the top of a column of 300 parts by volume silica gel and the column was first washed with 500 parts by volume of chloroform and then eluted with 500 parts by volume of chloroform-methanol (50:1), 500 parts by volume of chloroform-methanol (20:1) and 500 parts by volume of chloroform-methanol (10:1). The eluate was collected in 25 parts by volume fractions.

A 0.5 part by volume portion of each fraction was concentrated under reduced pressure. To the concentrate was added 0.05 part by volume of ethyl acetate, and the mixture as a sample was subjected to silica gel thin layer chromatography (developing system: chloroform-methanol=9:1).

The fractions Nos. 39 and 40 absorbing at 2537 Å in the zone of Rf 0.50–0.60 were collected and concentrated to dryness under reduced pressure. To the residue was added 2 parts by volume of ethyl acetate and the mixture was allowed to stand, whereupon 0.150 part crystals of Antibiotic C-15003 were obtained.

The above crystals of Antibiotic C-15003 (0.150 part) were dissolved in 15 parts by volume of methanol, followed by addition of 0.300 part of sodium chloride and 15 parts by volume of water. A column was packed with 200 parts by volume of Diaion HP-10 (Mitsubishi Kasei K.K.) and calibrated with 600 parts by volume of 50% methanol-water containing 5% of NaCl. The sample solution prepared above was passed through the column, and gradient elution was carried out using 1,500 parts by volume of 60% methanol-water containing 5% NaCl and 1,500 parts by volume of 95% methanol-water. The eluate was collected in 15 parts by volume fractions and each fraction was investigated by silica gel thin layer chromatography. The fractions 145 to 153 contained C-15003 P-3, the fractions 167–180 contained C-15003 P-3' and P-4 and the fractions 185–190 contained C-15003 P-4.

Each group of fractions was concentrated and dissolved by the addition of 50 parts by volume of water and 100 parts by volume of ethyl acetate. The solution was shaken in a separatory funnel and the water layer was separated and, after washing with two 50 parts by volume-portions of water, the ethyl acetate layer was dried over anhydrous sodium sulfate, concentrated and allowed to stand. In the above manner, crystals were obtained from each group of fractions. The crystals were collected by filtration and dried.

| | |
|---|---|
| C-15003 P-3 | 0.070 part |
| C-15003 P-3', P-4 | 0.018 part |
| C-15003 P-4 | 0.015 part |

The mixed crystals of C-15003 P-3' and P-4 (0.018 part) were dissolved in 0.3 part by volume of ethyl acetate and spotted in a line at a distance of 2.5 cm from the bottom edge of a silica gel glass plate (Merck, West Germany, Kieselgel 60 F$_{254}$ 0.25 mm, 20×20), followed by development with ethyl acetate-methanol (19:1). After development to about 18 cm, the absorption band at Rf 0.68 (P-4) and Rf 0.65 (P-3') were scrapped off and each was independently extracted twice with ethyl acetate containing a small amount of water. The resultant ethyl acetate extract was washed with water, dried over anhydrous sodium sulfate, concentrated under reduced pressure and allowed to stand.

0.010 Part crystals of C-15003 P-4 and 0.003 part crystals of C-15003 P-3' were obtained from the fractions of Rf 0.68 and Rf 0.65, respectively.

EXAMPLE 6

One thousand parts by volume of the culture of Example 2 was inoculated into a 200,000 parts by volume tank of stainless steel containing 100,000 parts by volume of a seed culture medium and the inoculated medium was incubated at 28° C. under aeration (100,000 parts by volume/min.) and agitation (200 r.p.m.) for 48 hours to prepare a seed culture. This seed culture was transferred to a 2,000,000 parts by volume tank of stainless steel containing 1,000,000 parts by volume of a fermentation medium similar to that used in Example 1 at a transplantation rate of 10%. Cultivation was carried out at 28° C. under aeration (1,000,000 parts by volume/min.), agitation [120 r.p.m. (1/3 DT)] and internal pressure (1 kg/cm$^2$) for 90 hours. The resultant culture was found to have a titer of 20 μg/ml as assayed by the assay procedure described in Example 1.

To 900,000 parts by volume of the above culture was added 900,000 parts by volume of acetone and, after an hour's stirring, 20,000 parts of Hyflo-Supercel (Johnes & Manville, U.S.A.) was added. The mixture was further stirred and filtered on a pressure filter machine.

To 1,700,000 parts by volume of the resultant filtrate was added 500,000 parts by volume of water and, in a Podbielniak (Podbielniak, Inc.), the mixture was extracted with 1,000,000 parts by volume of ethyl acetate. The ethyl acetate layer was washed with water, dried by the addition of anhydrous sodium sulfate and concentrated under reduced pressure. To the concentrate was added petroleum ether and the resultant precipitate was recovered by filtration and dried. By the above procedure was obtained 68 parts of crude product I. Thereafter, as in Examples 3, 4 and 5, this crude product was purified to obtain 9.5 parts of C-15003 P-3, 0.300 part of C-15003 P-3' and 2.5 parts of C-15003 P-4.

EXAMPLE 7

In 1 part by volume of tetrahydrofuran was dissolved 0.015 part of the Antibiotic C-15003 crystals obtained in Example 5 and after the solution was cooled to −5° C., 0.012 part of lithium aluminum hydride was added. The mixture was allowed to stand for 2 hours. Following the addition of 0.5 part by volume of a 1% aqueous solution of $H_2SO_4$, the reaction mixture was extracted with 2 parts by volume of ethyl acetate. The ethyl acetate layer was washed with water, dried by the addition of anhydrous sodium sulfate and concentrated under reduced pressure. Preparative TLC with silica gel was carried out on the concentrate and the zone of Rf 0.25 to 0.3 was scraped off and extracted with ethyl acetate containing a small amount of water. The extract was washed with water, dried over anhydrous sodium sulfate and concentrated under reduced pressure, whereupon crystals separated. The crystals were recovered by filtration and dried. By the above procedure was obtained 0.010 part of P-15003 P-0, melting point 174° C.

Elemental analysis: Found C,59.65; H, 6.58; N, 5.02; Cl, 6.51; calcd. for $C_{28}H_{37}ClN_2O_8$ C, 59.52; H, 6.60, N, 4.96; Cl, 6.27.

IR: 1715, 1670, 1580(cm$^{-1}$)

UV(nm): 232(32750), 244(sh, 30850), 252(31650), 281(5750), 288(5700)

In properties, this product is identical with maytansinol.

What we claim is:

1. A method for producing Antibiotic C-15003 which has the general formula:

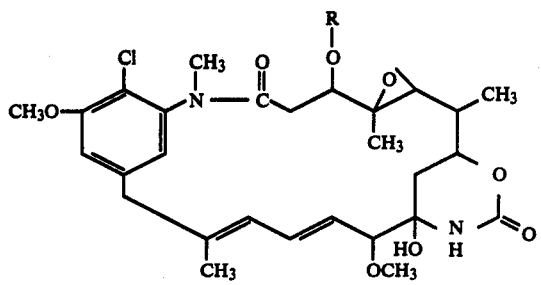

wherein R represents

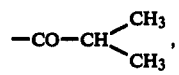

$-CO-CH_2-CH_2-CH_3$ or

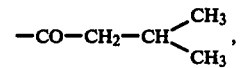

which comprises cultivating a microorganism belonging to the genus Nocardia and being capable of producing Antibiotic C-15003 in a culture medium containing assimilable carbon sources and digestible nitrogen sources until Antibiotic C-15003 is substantially accumulated therein, and recovering Antibiotic C-15003.

2. A method as claimed in claim 1, wherein the microorganism is Nocardia No.C-15003 (ATCC 31281; IFO 13726; FERM 3992) or its mutants or variants thereof.

* * * * *

UNITED STATES PATENT AND TRADEMARK OFFICE
CERTIFICATE OF CORRECTION

PATENT NO. : 4,162,940
DATED : July 31, 1979
INVENTOR(S) : Eiji HIGASHIDE, Mitsuko ASAI and SEIICHI TANIDA It is certified that error appears in the above-identified patent and that said Letters Patent are hereby corrected as shown below:

On the front page of the patent, item [56], line 2 under "Other Publications", after "1354-1356", please insert -- and vol. 97, --;

Column 13, line 40, change "5294-5215" to -- 5294-5295 --;

Column 17, line 25, change "P-15003 P-0" to -- C-15003 P-0 --.

Signed and Sealed this

Twenty-ninth Day of July 1980

[SEAL]

Attest:

SIDNEY A. DIAMOND

Attesting Officer          Commissioner of Patents and Trademarks